(12) United States Patent
Zeidan et al.

(10) Patent No.: US 10,542,888 B2
(45) Date of Patent: Jan. 28, 2020

(54) INTERACTIVE DISPLAY OF SELECTED ECG CHANNELS

(71) Applicant: Biosense Webster (Israel) Ltd., Yokneam (IL)

(72) Inventors: Ziyad Zeidan, Zemmer (IL); Gal Hayam, Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 39 days.

(21) Appl. No.: 15/722,667

(22) Filed: Oct. 2, 2017

(65) Prior Publication Data

US 2019/0099078 A1     Apr. 4, 2019

(51) Int. Cl.
| | | |
|---|---|---|
| *A61B 5/00* | (2006.01) | |
| *A61N 1/37* | (2006.01) | |
| *A61N 1/372* | (2006.01) | |
| *G16H 40/63* | (2018.01) | |
| *A61N 1/04* | (2006.01) | |

(52) U.S. Cl.
CPC .......... *A61B 5/0006* (2013.01); *A61N 1/3702* (2013.01); *A61N 1/37247* (2013.01); *A61N 1/0404* (2013.01); *G16H 40/63* (2018.01)

(58) Field of Classification Search
CPC ..... A61B 5/0006; A61B 5/0402; A61B 5/044; A61B 5/742–7435; A61N 1/37247; A61N 1/3702; A61N 1/0404; G16H 40/63
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 5,944,022 A | 8/1999 | Nardella et al. |
| 5,983,126 A | 11/1999 | Wittkampf |
| 6,172,499 B1 | 1/2001 | Ashe |
| 6,177,792 B1 | 1/2001 | Govari et al. |
| 6,266,551 B1 | 7/2001 | Osadchy et al. |

(Continued)

FOREIGN PATENT DOCUMENTS

WO     2008-136008 A2     11/2008

OTHER PUBLICATIONS

Extended European Search Report dated Feb. 4, 2019 for the European Patent Application No. 18198039.2.

*Primary Examiner* — Scott M. Getzow
(74) *Attorney, Agent, or Firm* — Volpe and Koenig, P.C.

(57) ABSTRACT

An ECG signal correlation and display system is provided which includes memory configured to store ECG data corresponding to electrical signals, acquired over time, from different areas of a heart and location data corresponding to acquired location signals indicating locations of the different areas of the heart from which the electrical signals are acquired. The system also includes a processing device configured to generate, from the ECG data and the location data, mapping information for displaying a map of the heart and determine a location of an anatomical region of the heart on the map. The processing device is also configured to determine which of the plurality of electrical signals are acquired from the anatomical region of the heart and generate correlated ECG signal information for displaying the electrical signals determined to be acquired from the anatomical region of the heart.

14 Claims, 9 Drawing Sheets

(56) References Cited

U.S. PATENT DOCUMENTS

| | | |
|---|---|---|
| 6,456,828 B1 | 9/2002 | Ozluturk |
| 6,690,963 B2 | 2/2004 | Ben-Haim et al. |
| 6,788,967 B2 | 9/2004 | Ben-Haim et al. |
| 2006/0116576 A1 | 6/2006 | McGee et al. |
| 2009/0069704 A1 | 3/2009 | MacAdam et al. |
| 2009/0093806 A1 | 4/2009 | Govari et al. |
| 2009/0138007 A1 | 5/2009 | Govari et al. |
| 2011/0206256 A1* | 8/2011 | Ramanathan ...... A61B 5/04021 382/128 |
| 2012/0030255 A1 | 2/2012 | Xue et al. |
| 2014/0005563 A1 | 1/2014 | Ramanathan et al. |

* cited by examiner

INTERACTIVE DISPLAY OF SELECTED ECG CHANNELS

SUMMARY

The present application provides an electrocardiogram (ECG) signal correlation and display system including memory and a processing device. The memory is configured to store ECG data corresponding to electrical signals, acquired over time, from different areas of a heart and location data corresponding to acquired location signals indicating locations of each of the different areas of the heart from which the electrical signals are acquired. The processing device is configured to generate, from the ECG data and the location data, mapping information for displaying a map of the heart. The processing device is also configured to determine a location of an anatomical region of the heart on the map and determine which of the plurality of electrical signals are acquired from the anatomical region of the heart. The processing device is further configured to generate correlated ECG signal information for displaying the electrical signals determined to be acquired from the anatomical region of the heart.

The present application provides an ECG signal correlation and display method that includes acquiring ECG data, corresponding to a plurality of electrical signals of a heart acquired over time, via a plurality of electrodes disposed at different areas of the heart and acquiring location data, corresponding to acquired location signals indicating locations of each of the different areas of the heart from which the electrical signals are acquired. The method also includes generating, from the ECG data and the location data, mapping information for displaying a map of the heart and determining a location of an anatomical region of the heart on the map. The method further includes determining which of the plurality of electrical signals are acquired from the anatomical region of the heart and generating correlated ECG signal information for displaying the electrical signals determined to be acquired from the anatomical region of the heart.

The present application provides a non-transitory computer readable medium, comprising instructions for causing a computer to execute an ECG signal selection and display method. The instructions include acquiring ECG data, corresponding to a plurality of electrical signals of a heart acquired over time, via a plurality of electrodes disposed at different areas of the heart and acquiring location data, corresponding to acquired location signals indicating locations of each of the different areas of the heart from which the electrical signals are acquired. The instructions also include generating, from the ECG data and the location data, mapping information for displaying a map of the heart and determining a location of an anatomical region of the heart on the map. The instructions further include determining which of the plurality of electrical signals are acquired from the anatomical region of the heart and generating correlated ECG signal information for displaying the electrical signals determined to be acquired from the anatomical region of the heart.

BRIEF DESCRIPTION OF THE DRAWINGS

A more detailed understanding can be had from the following description, given by way of example in conjunction with the accompanying drawings wherein.

DETAILED DESCRIPTION

Figure 1:
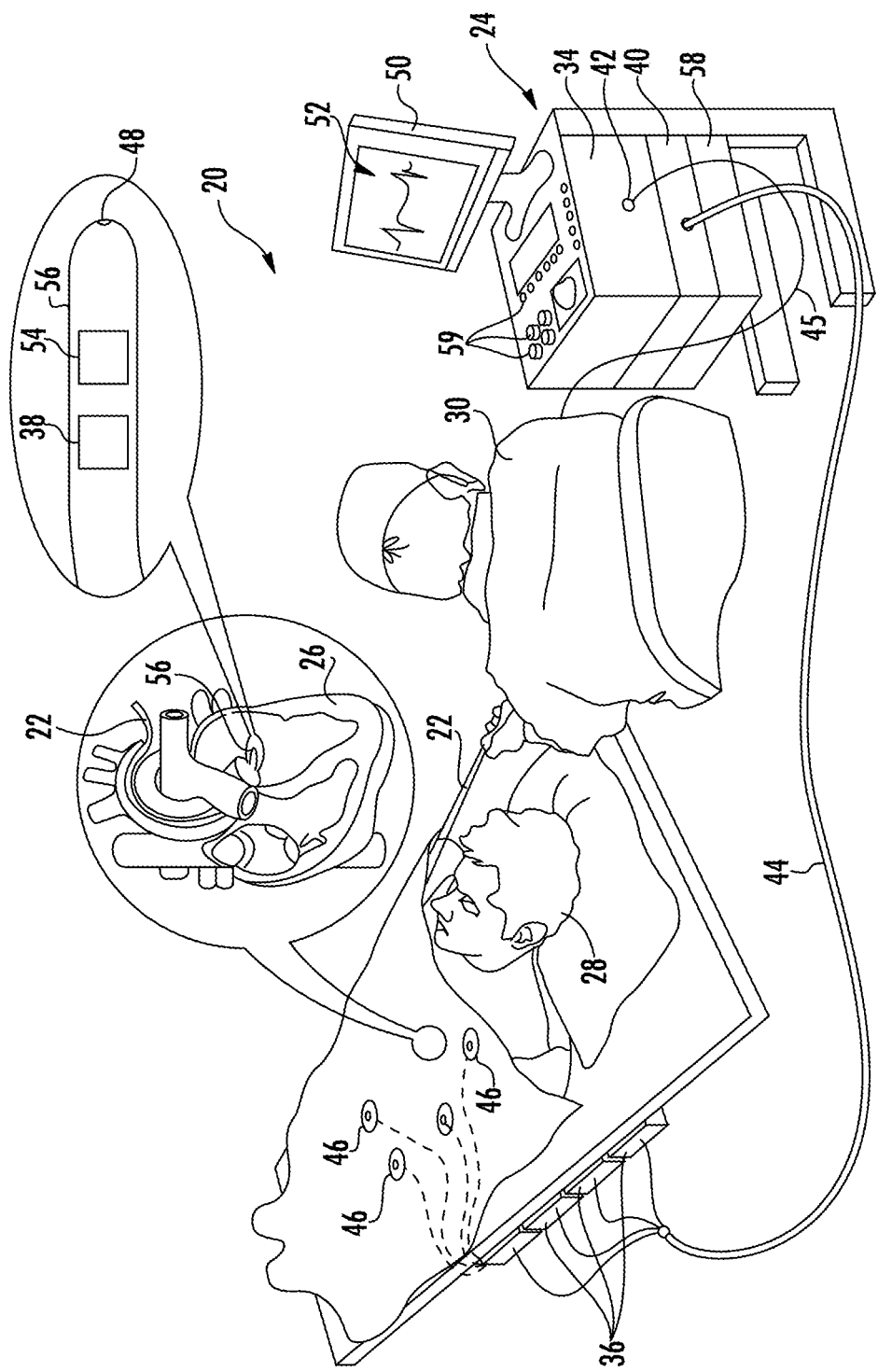
FIG. 1 is an illustration of an example medical system for navigating a tool in 3-D space according to embodiments disclosed herein.

Conventional methods and systems used for catheter ablation typically include inserting the catheter through an incision in the skin and guided up to the heart. Before ablation is performed, intra-cardiac (IC) electrocardiogram (ECG) signals of the heart are acquired (i.e., recorded for a period of time, such as 20 to 30 seconds) via a plurality of electrodes placed at different areas of the heart. The signals are monitored and used to provide information to determine whether one or more areas of the heart are causing the irregular heart rhythm. For example, dynamic maps of the heart are created from the ECG signals acquired via the electrodes and location information indicating locations of the electrodes in a three dimensional (3D) space. Based on a visual assessment of these dynamic maps, a region of interest (ROI) of the heart is determined which may include an area of the heart causing an irregular heart rhythm and be targeted for ablation. The conventional methods and systems used to determine areas to be ablated, however, are time consuming (e.g., several hours) and rely on medical personnel with specific expertise and experience (typically requiring many hours of training).

For example, determination of these areas to be ablated depends upon correlation between a visualized ROI, the map (i.e., the displayed anatomical region) and the corresponding ECG signals. The correlation is based on identification of the electrodes located at the ROI (i.e., at the anatomical surface defining the visual ROI). Because of visual overlap between proximal electrodes (i.e., electrodes at the visualized surface the ROI) and distal electrodes (i.e., electrodes at the opposing surface of the ROI), however, the ECG signals associated with the ROI are often difficult to visually identify. In some conventional techniques identification of the ECG signals associated with the ROI includes changing (e.g., turning, rotating) the orientation of the displayed anatomical region such that anatomical region is viewed from different perspectives to determine which electrodes are projected on the visualized surface of the ROI and which electrodes are projected on the opposing surface. Additional time is incurred, however, to view the mapped anatomical region from the different perspectives.

Embodiments disclosed herein provide systems, apparatuses and methods used to facilitate efficient determination of areas to be ablated by displaying a smaller number of ECG signals, which correspond to an identified ROI, rather than displaying each of the ECG signals acquired by each of the electrodes disposed on the heart. For example, a location of an anatomical region of the heart on the 3D map is determined from user input. The ECG signals which correspond to areas of the heart located within the anatomical region are determined and displayed and the ECG signals determined to correspond to areas of the heart that are not located within the anatomical region are prevented from being displayed. Because a smaller number of ECG signals are displayed, it is easier for a user viewing the ECG signals to determine activation sequences or patterns in the ROI from the displayed ECG signals.

Mapping techniques described herein utilize various parameters (e.g., cycle, earliness, R-S complex, conduction velocity (CV), block and fractionation) of acquired IC ECG signals and detected local activation times (LATs) to identify potential evidence of sources of activation (i.e., drivers) and perpetuators of the AF substrate. Evidence identifying potential drivers is used to provide the mapping of the AF substrate. Drivers are classified by their spatio-temporal manifestation types, such as focal sources, which originate at a small area of the atria and spread centrifugally from a single point and localized rotational activation (LRA) sources or rotational activation patterns (RAPs) sources, which are irregular regions of the heart where the electrical pulses rotate at least 360 degrees about a center area.

Embodiments described herein include correlating between dynamic activation maps and ECG signals associated with ROIs, enabling efficient review of ROIs and identification of the electrodes associated with the ROIs to facilitate the determination of potential sources of activation (i.e., potential drivers), such as focal sources and RAPs.

Referring now to FIG. 1, an illustration of an example medical system 20 is shown that may be used to generate and display information 52 (e.g., anatomical models of a portion of a patient and signal information). Tools such as tool 22, can be any tool used for diagnostic or therapeutic treatment, such as for example, a catheter (such as catheter 202 illustrated in FIG. 2 and described in more detail below) having a plurality of electrodes for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine 3-D position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 1 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The tool 22 may also include a force sensor 54 contained within the tip 56. The force sensor 54 may measure a force applied by the tool 22 (e.g., the tip 56 of the tool) to the endocardial tissue of the heart 26 and generate a signal that is sent to the control console 24. The force sensor 54 may include a magnetic field transmitter and a receiver connected by a spring in the tip 56, and may generate an indication of the force based on measuring a deflection of the spring. Further details of this sort of probe and force sensor are described in U.S. Patent Application Publications 2009/ 0093806 and 2009/0138007, whose disclosures are incorporated herein by reference. Alternatively, the tip 56 may include another type of force sensor that may use, for example, fiber optics or impedance measurements.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

Although the example medical system 20 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on the electrical impulses received from the body surface electrodes 46 and the electrical signals received from the tool 22 via the I/O interface 42 and other components of medical system 20, the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit (WTRU) enabling local digital signal processing, a radio link, and a miniaturized rechargeable battery. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is exemplary. Any suitable configuration of the medical system 20 may be used and implemented.

Figure 2:
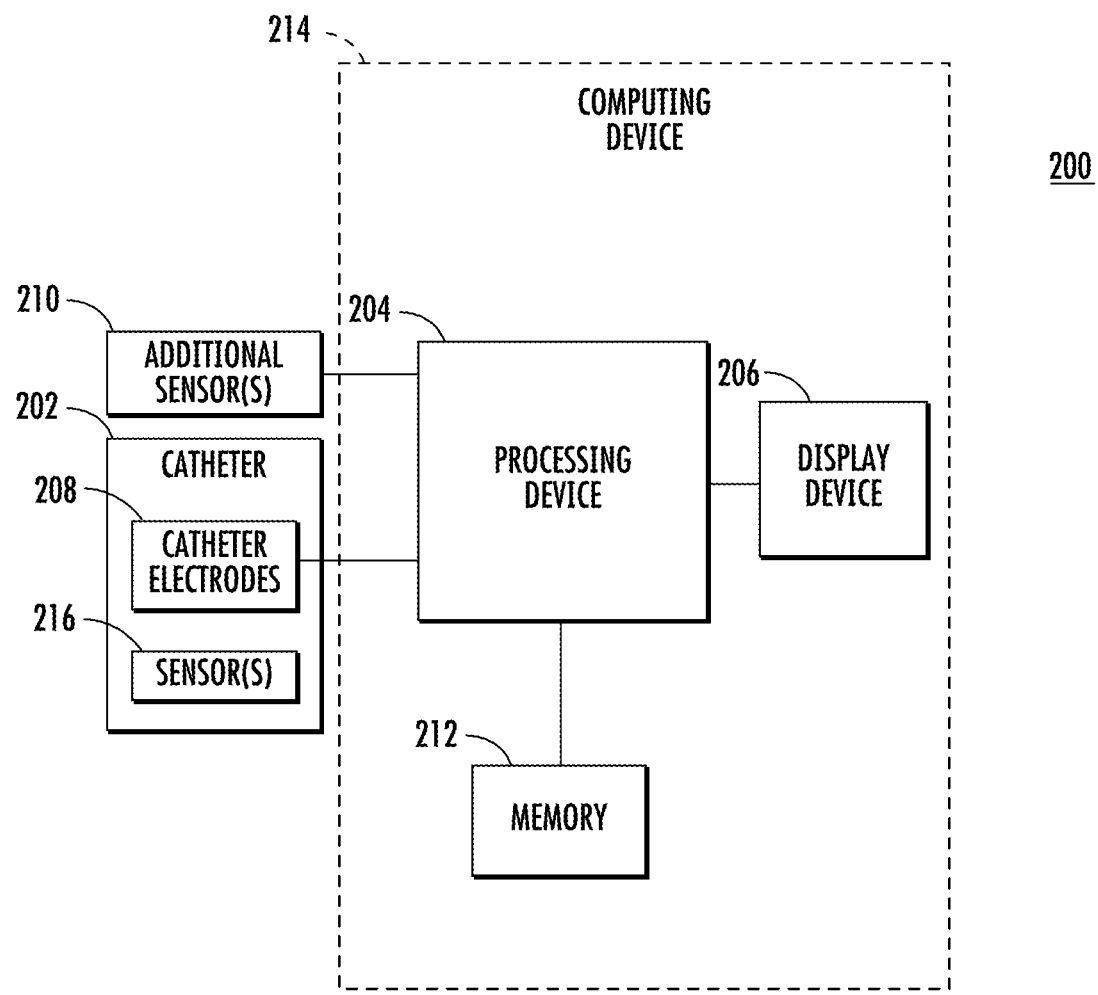
FIG. 2 is an illustration of components of an example medical system for use with embodiments described herein.

FIG. 2 is a block diagram illustrating example components of a medical system 200 for use with embodiments described herein. As shown in FIG. 2, the system 200 includes a catheter 202, a processing device 204, a display device 206 and memory 212. The processing device 204, display device 206 and memory 212 are a part of computing device 214. In some embodiments, the display device 206 may be separate from computing device 214. Computing device 214 may also include an I/O interface, such as I/O interface 42 shown in FIG. 1

Catheter 202 includes an array of catheter electrodes 208 each configured to detect electrical activity (electrical signals) of an area of the heart over time. When an ECG is performed, each electrode detects the electrical activity of an area of the heart in contact with the electrode. Catheter 202 also includes one or more sensors (e.g., sensor(s) 216), which include, for example, a magnetic field location sensor (e.g., sensor 38 in FIG. 1) for providing location signals to indicate the 3-D position coordinates of the catheter 202. In some procedures, one or more additional sensors 210 that are separate from the catheter 202, as shown in example system 200, are also used to provide location signals. Additional sensors 210 may also include sensors (e.g., electrodes on the skin of a patient) used to assist with detection of electrical activity of the heart via detection of electrical changes on the skin due to the electro-physiologic pattern of the heart.

Processing device 204 may include one or more processors each configured to process the ECG signals, record ECG signals over time, filter ECG signals, fractionate ECG signals into signal components (e.g., slopes, waves, complexes) and generate and combine ECG signal information for displaying the plurality of electrical signals on display device 206. Processing device 204 may also generate and interpolate mapping information for displaying maps of the heart on display device 206. Processing device 204 may include one or more processors (e.g., signal processor 40) configured to process the location information acquired from sensors (e.g., additional sensor(s) 210 and catheter sensor(s) 216) to determine the position coordinates of the catheter 202, including both location and orientation coordinates.

In addition, as described in more detail below, processing device 204 determines locations of anatomical regions of the heart on the map, determines which electrical signals correspond to areas of the heart that are located within the anatomical regions of the heart and generates correlated ECG signal information for displaying electrical signals determined to correspond to the areas of the heart that are located within the anatomical regions of the heart (i.e., determined to be the electrical signals acquired by electrodes (i.e., poles) disposed at the corresponding areas of the heart). Processing device 204 drives display device 206 to display dynamic maps (i.e., spatio-temporal maps) of the heart and the electrical activity of the heart using the mapping information and the ECG data. Processing device 204 also drives display device 206 to display the ECG signals determined to be located within the anatomical region of the heart using the correlated ECG signal information.

Display device 206 may include one or more displays each configured to display maps of the heart representing spatio-temporal manifestations of the electrical activity of the heart over time and display the ECG signals acquired from the heart over time. For example, a map of the heart, representing the electrical activity of the heart for a specific time interval and the ECG signals acquired from the heart during the time interval, may be displayed concurrently on the same display device. Alternatively, the map of the heart and the ECG signals acquired during the same time interval may be displayed on separate display devices.

The catheter electrodes 208, catheter sensor(s) 216 and additional sensor(s) 210 may be in wired or wireless communication with processing device 204. Display device 206 may also be in wired or wireless communication with processing device 204.

Figure 3:
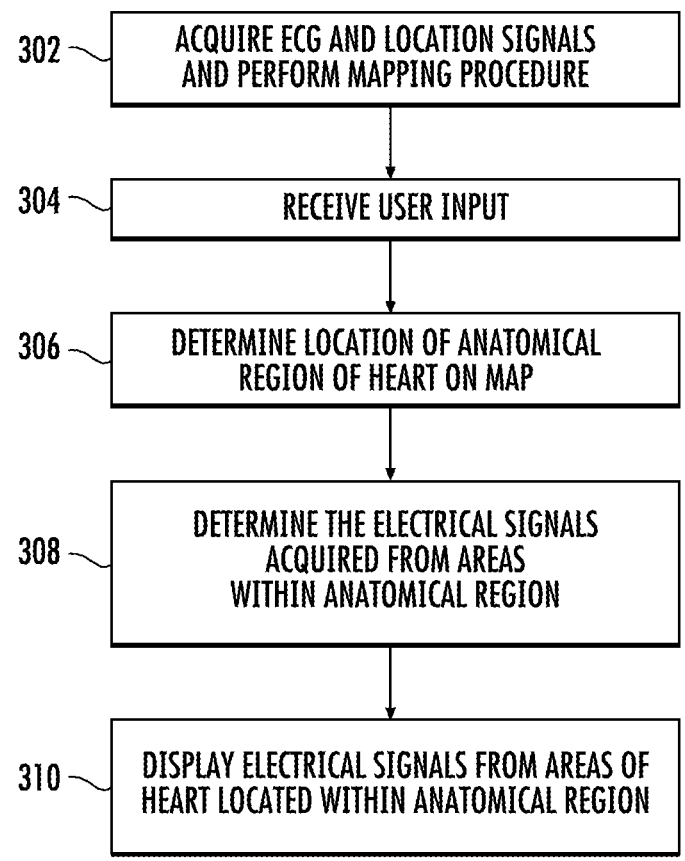
FIG. 3 is a flow diagram illustrating an exemplary ECG signal correlation and display method according to an embodiment disclosed herein.

FIG. 3 is a flow diagram illustrating an exemplary ECG signal correlation and display method 300. As shown in block 302, the method 300 includes acquiring ECG signals and location signals and performing a mapping procedure. The electrical signals are acquired, for example, over time from different areas of a heart via a plurality of electrodes disposed at the different areas of the heart. Any number of electrodes may be used to acquire the electrical signals. The location signals are acquired from any number of sensors (e.g., sensors on a catheter and sensors separate from the catheter) used to indicate the locations of each of the different areas of the heart via the locations of the catheter and electrodes in 3D space.

A mapping procedure is performed which includes the display of dynamic maps of the heart in 3D space based on the acquired electrical signals and location signals. The dynamic maps illustrate the heart in 3D space and its corresponding electrical activity over time. The mapping procedure may also include processing the electrical signals and location signals as ECG data and location data, respectively, and storing the ECG data and location data in memory. During the mapping procedure, the electrical signals, acquired over predetermined time intervals from the heart, are also displayed for each of the electrodes (i.e., poles).

Figure 4:
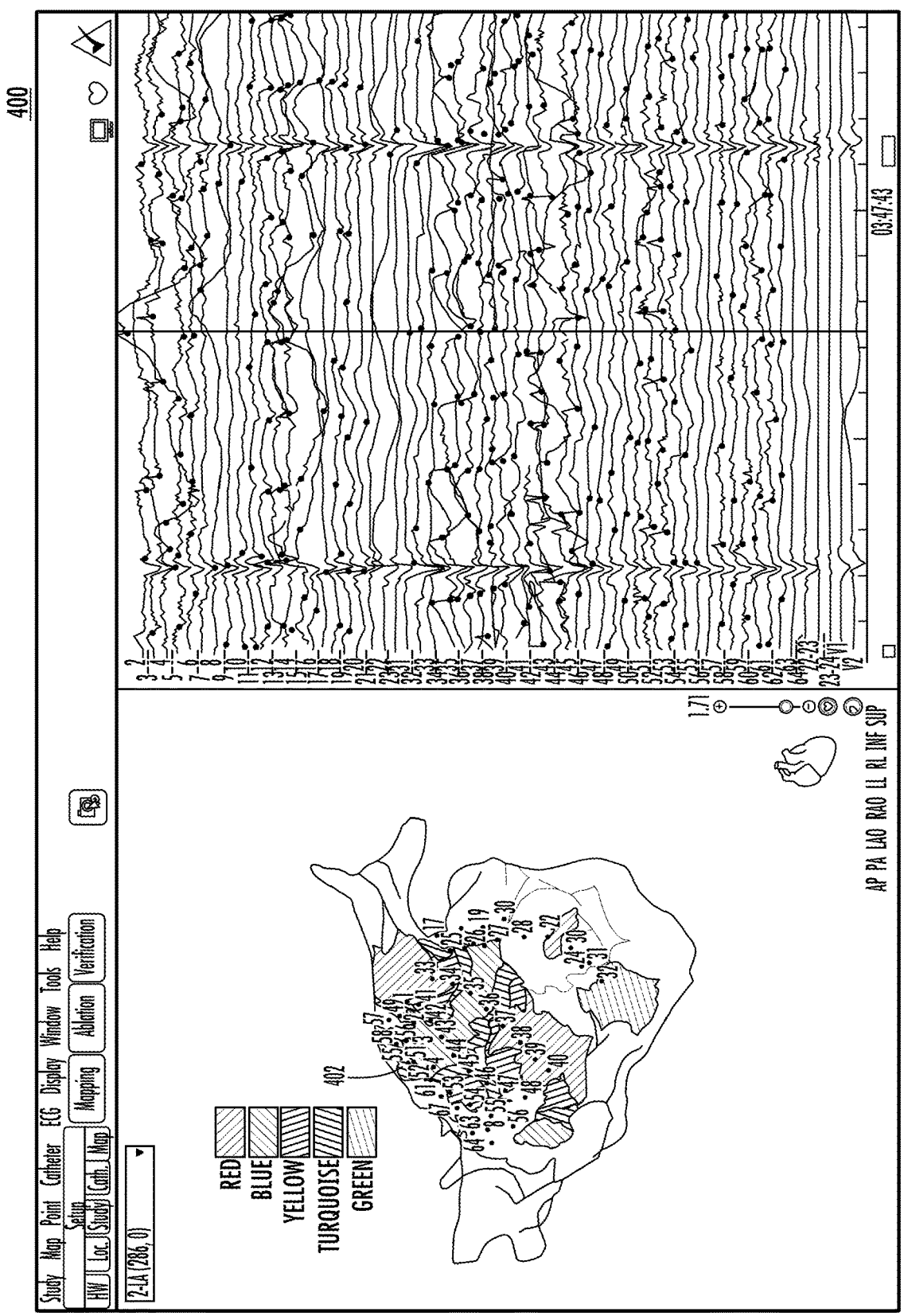
FIG. 4 shows an example display of a map of a heart and electrical signals acquired from the heart over a predetermined time interval according to embodiment disclosed herein.

FIG. 4 is an illustration of an example display 400 of a map of a heart 402 (shown in the map window 404) and the corresponding electrical signals (shown in ECG window 406) acquired from the heart 402, via a plurality of electrodes over a predetermined time interval. The example display 400 shown at FIG. 4 corresponds to a procedure in which 64 electrodes are used to acquire electrical signals from different areas of the heart 402. The number of electrodes illustrated in FIG. 4, however, is merely exemplary. Any number of electrodes (e.g., 100 or more electrodes) may be used to acquire electrical signals from a heart.

As shown in display 400, the electrical activity of different areas of the heart 402 is illustrated using different visual indicator types. The indicator types (e.g., hash lines shown in FIG. 4) are merely exemplary. The electrical activity of different areas may be indicated using other types of visual indicators, such as for example, shading or colors (e.g., such as the colors shown next to corresponding hashed lines in the map window 404). The locations of the electrodes on the heart 402 are also shown in display 400.

Based on the displayed electrical activity of the heart 402, a user (e.g., physician) may determine (e.g., visualize) a ROI (i.e., an anatomical region of the heart 402) of the heart 402 as potentially causing an irregular heart rhythm and, therefore, be a potential region targeted for ablation. As can be seen from the map of the heart 402, however, there is a visual overlap between proximal electrodes (i.e., electrodes at the surface in the foreground in display 400) and distal electrodes (i.e., electrodes at the opposing surface of the ROI). Accordingly, the ECG signals associated with a ROI are difficult to visually identify. In addition, the ECG signals corresponding to each of the electrodes (minus electrodes 24-30 which may acquire false readings or no signals were acquired) are displayed in ECG window 406. As can be seen in the ECG window 406, it may be difficult to correlate between the visualized ROI on the map and the ECG signals which correspond to the visualized ROI because of the large number of ECG signals displayed in the ECG window 406, most of which may not correspond to electrodes at the ROI.

Referring again to FIG. 3, as shown in block 304, the method 300 includes receiving a user input. For example, based on a determined visualized ROI, a user may provide input indicating a location of the ROI on the map of the heart. The user input may include a marked area (e.g., line or shape) on a surface of the heart 402 (e.g., received via an input device, such as a mouse, or via touch screen capability), as described in more detail below with regard to FIGS. 5 and 6. Alternatively, the user input may include an indication of a location of a two dimensional (2D) plane on the map of the heart to indicate the ROI (i.e., an anatomical region of the heart 402 on the map), such as 2D plane 802 described in more detail below with regard to FIGS. 8 and 9.

Based on the user input received at block 304, the method 300 includes determining the location of the anatomical region of the heart 402, as shown in block 306, determining which electrical signals are acquired from the anatomical region of the heart 402, as shown at block 308, and displaying the electrical signals determined to be acquired from the anatomical region of the heart 402, as shown at block 310.

Figure 5:
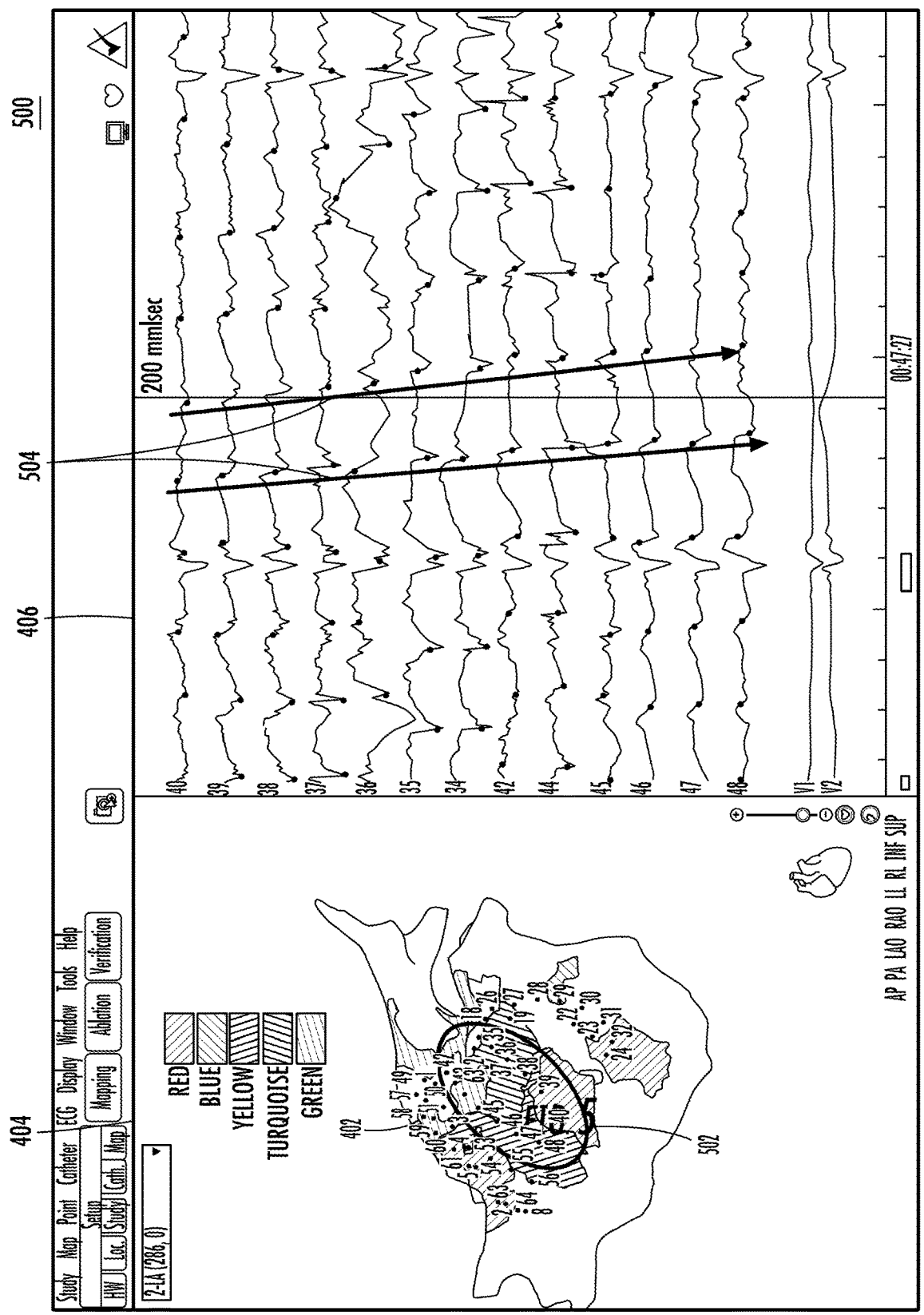
FIG. 5 shows an example display of a marked area on the map of heart shown in FIG. 4 and the corresponding electrical signals acquired from areas of the heart located in the marked area.
Figure 6:
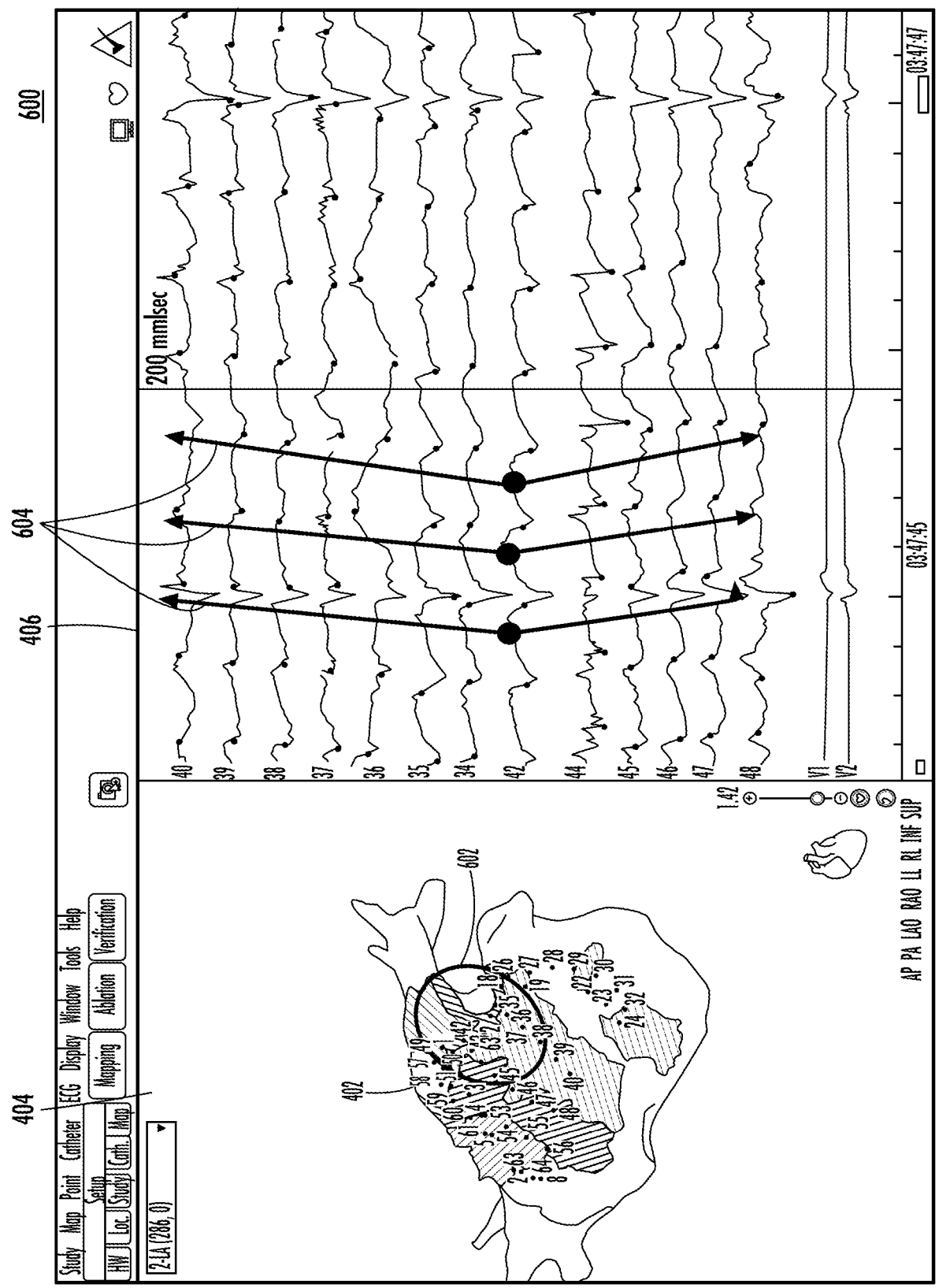
FIG. 6 shows an example display of a marked area on the map of heart shown in FIGS. 4 and 5 and the corresponding electrical signals acquired from areas of the heart located in the marked area.
Figure 7:
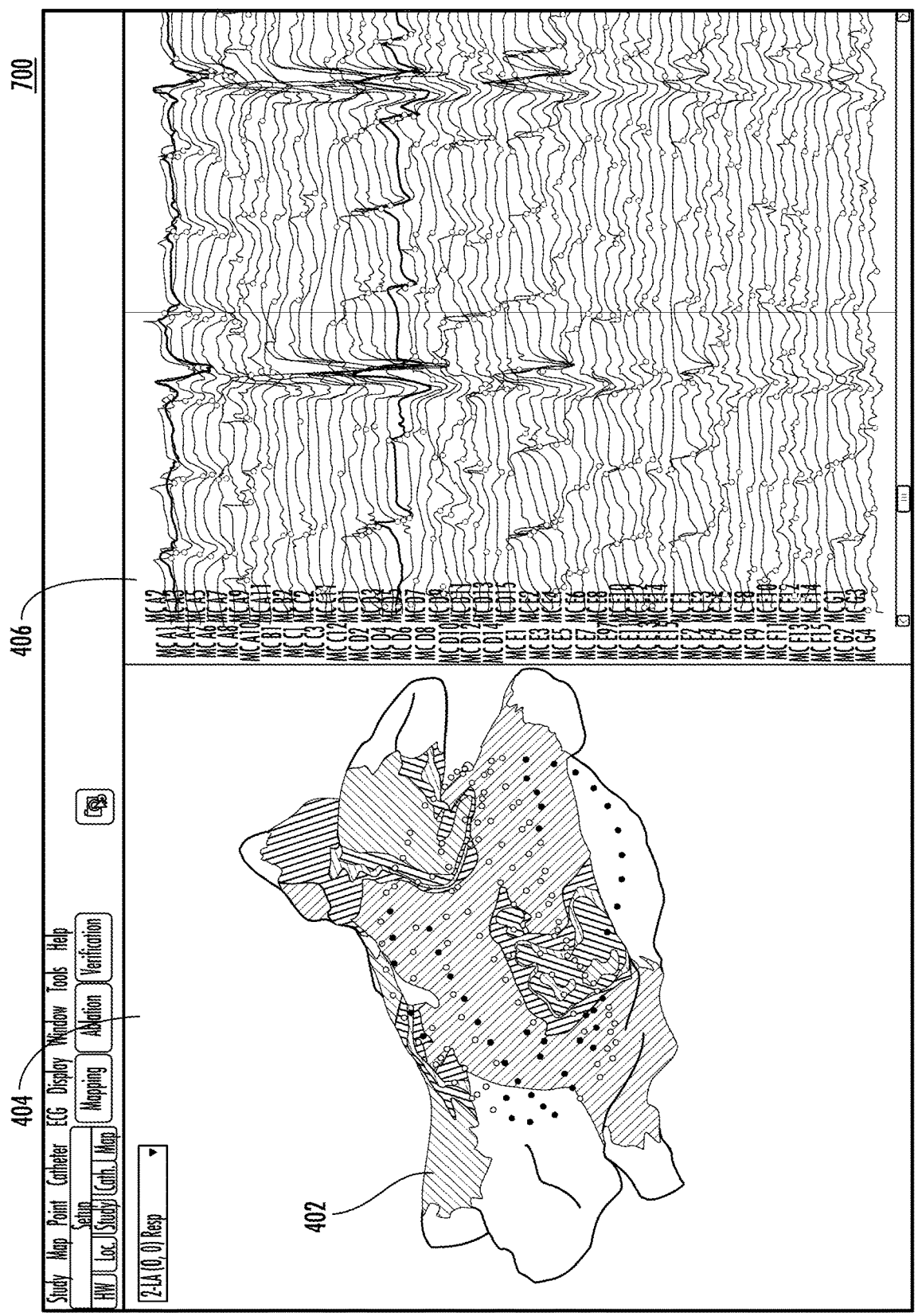
FIG. 7 shows an example display of a map of a heart and the electrical signals acquired from the heart over a predetermined time interval.
Figure 8:
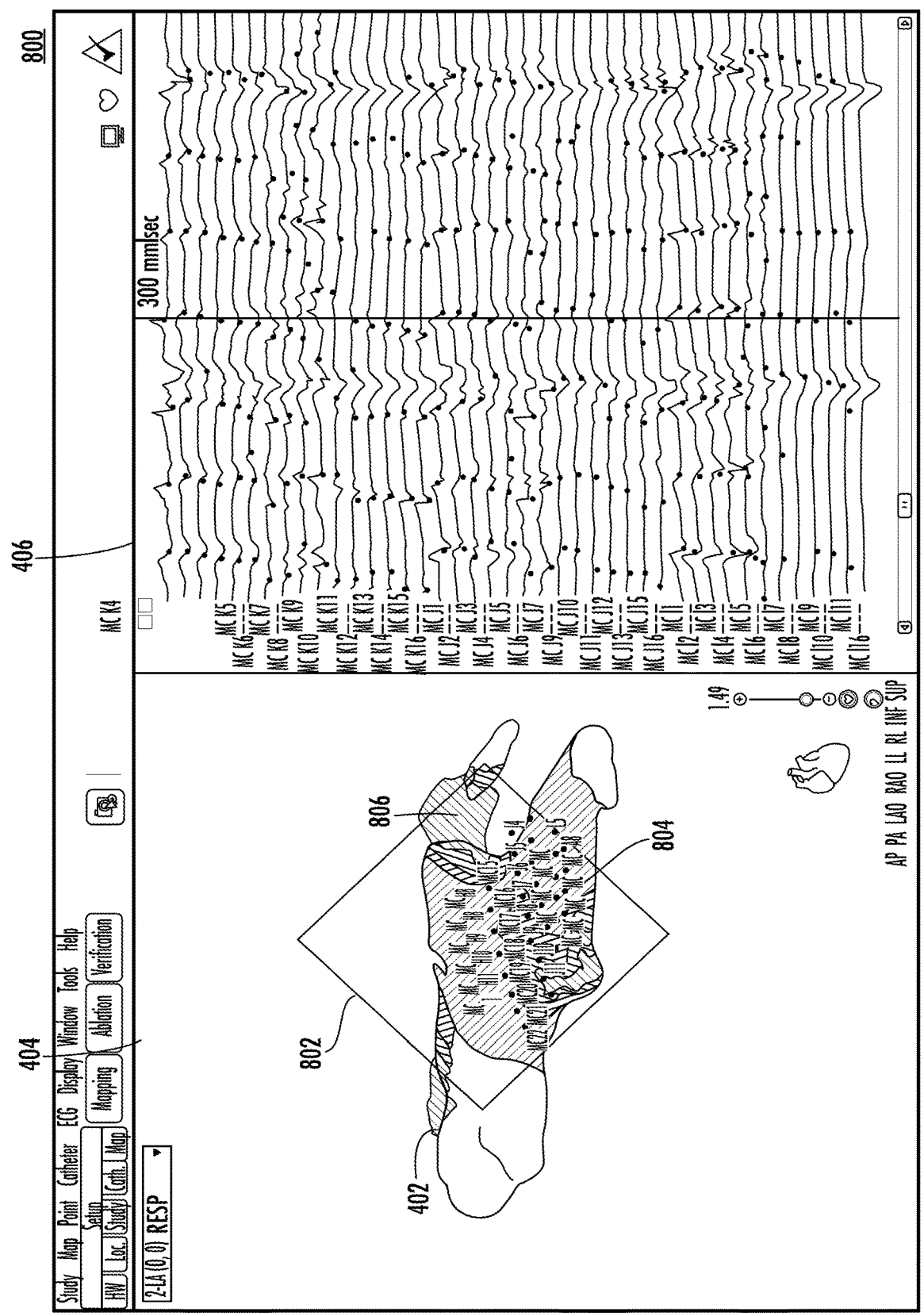
FIG. 8 shows an example display which includes a 2D plane at a first position used to define an anatomical region of the heart shown in FIG. 7 and the electrical signals acquired from areas of the heart located in the 2D plane.
Figure 9:
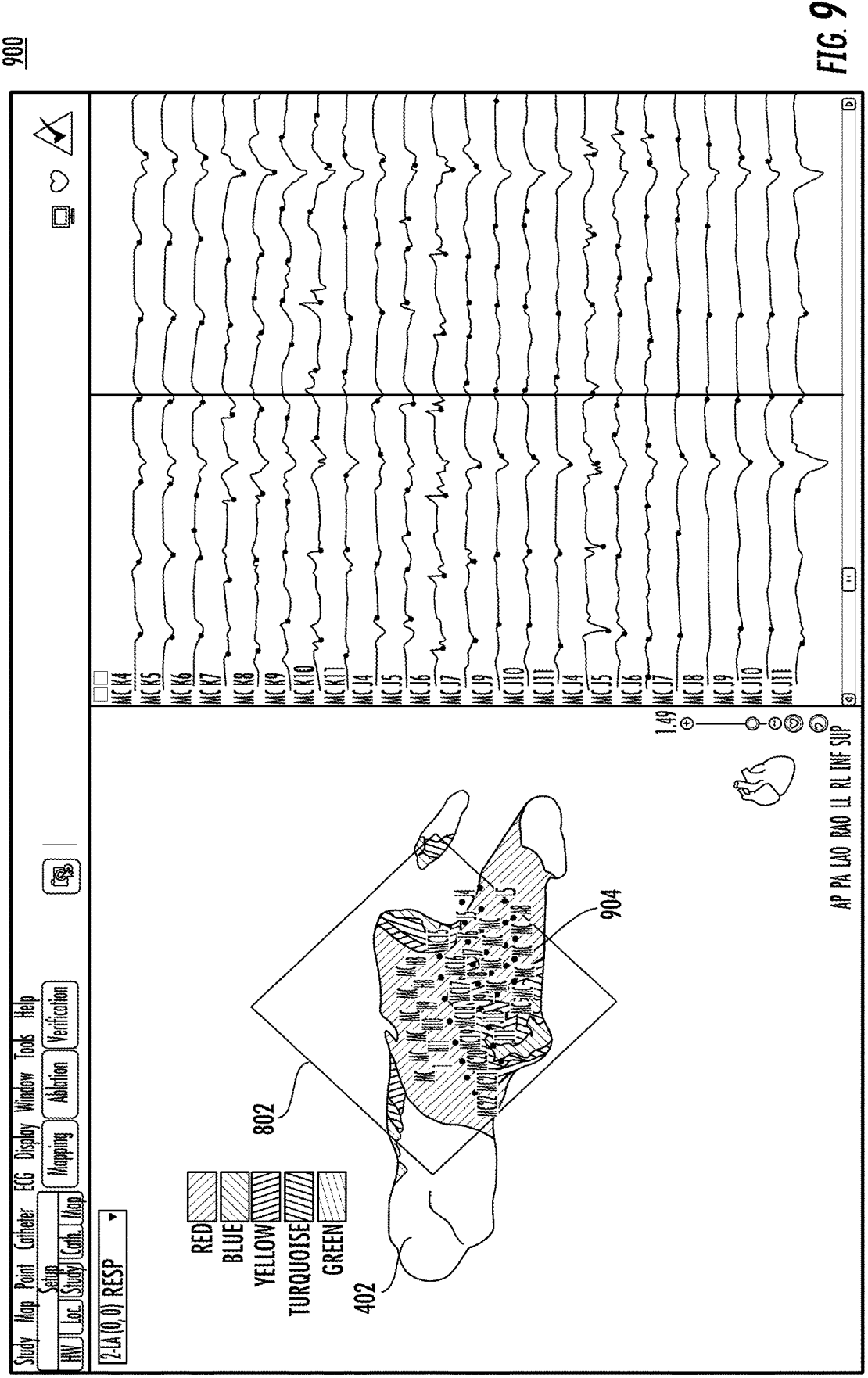
FIG. 9 shows an example display which includes the 2D plane at a second position used to define a second anatomical region of the heart shown in FIG. 8 and the electrical signals acquired from areas of the heart located in the 2D plane.

Two separate examples of the process shown in blocks 304 to 310 are now described. In the first example, FIGS. 4-6 are used to illustrate changes in the number of displayed ECG signals according to the number of areas of the heart 402 that are located in the anatomical region of the heart indicated by marked areas (e.g., marked areas 502 in FIGS. 5 and 602 in FIG. 6). In the second example, FIGS. 7-9 are used to illustrate changes in the number of displayed ECG signals based on the number of areas of the heart 402 that are located in the anatomical region of the heart 402 defined by a 2D plane (e.g., plane 802 in FIGS. 8 and 9).

With reference to the first example, as described above, the example display 400 shown at FIG. 4 corresponds to a procedure in which 64 electrodes are used to acquire electrical signals from different areas of the heart 402. As shown in the ECG window 406 of display 400, the electrical signals acquired by the 64 electrodes are displayed.

FIG. 5 is an illustration of an example display 500 of a marked area 502 on the map of heart 402 shown in FIG. 4 and the corresponding electrical signals acquired from areas of the heart 402 located in the marked area 502. The oval shape of the marked area 502 in FIG. 5 is merely exemplary. Marked areas may include any type of shape, including a line, to indicate the location of a ROI on a surface of the heart. Marked areas may be positioned on a map via an input device, such as a mouse or keyboard. In some embodiments, display devices may include touch screens and the marked areas may be positioned on a map via the touch screens of the display devices.

In addition to the marked area 502 in display 500, the view (i.e., orientation) of the heart 402 in FIG. 5 is slightly changed from the view (i.e., orientation) of the heart 402 shown in FIG. 4. A user may change views, for example, by rotating the heart 402 about an axis (not shown). The axis may be a horizontal axis, a vertical axis or an axis in any direction in 3D space. Accordingly, a user may rotate the heart 402 in any direction between 0 and 360 degrees in 3D space. For example, a user may rotate the heart 402 about an axis from the view of the heart 402 in FIG. 4 to the view of the heart 402 shown in FIG. 5.

Based on the displayed electrical activity of the heart 402 in the view shown in FIG. 5, a user may determine (e.g., visualize) a ROI (i.e., an anatomical region of the heart 402) as potentially causing an irregular heart rhythm and, therefore, be a potential region targeted for ablation. Accordingly, the user may indicate the location of the anatomical region of the heart by a marked area, such as the marked area 502 shown in FIG. 5.

The location of the anatomical region of the heart may be determined from the position of the marked area 502. The electrical signals acquired at the anatomical region are then determined and correlated ECG signal information is generated for displaying the electrical signals acquired at the anatomical region. The correlated ECG signal information may be provided to a display device (e.g. 206) via a wired medium, or wirelessly, via a wireless network.

The electrical signals, determined to be acquired at the anatomical region of the heart 402, are then displayed. For example, as shown in the display 500 at FIG. 5, the ECG window 406 has been changed to display 14 electrical signals (instead of the 60 electrical signals shown in FIG. 4) corresponding to the electrical signals acquired, via 14 electrodes, from the anatomical region of the heart 402 defined by the marked area 502. Accordingly, because a smaller number of electrical signals are displayed, it is easier to determine activation sequences or patterns in the ROI from the displayed electrical signals. For example, as indicated by the lines 504 in the ECG window 406 in FIG. 5, a source of activation, such as a focal source may be more easily identified by viewing the electrical signals in the ECG window 406.

FIG. 6 is an illustration of an example display 500 of a marked area 602 on the map of heart 402 shown in FIGS. 4 and 5 and the corresponding electrical signals acquired from areas of the heart 402 located in the marked area 602. As shown in FIGS. 5 and 6, the view (i.e., orientation) of the heart 402 in FIG. 6 is slightly changed from the view (i.e., orientation) of the heart 402 shown in FIG. 5. In addition, the shape and location of marked area 602 on the map of heart 402 in FIG. 6 is different from the shape and location of the marked area 502 on the map of heart 402 in FIG. 5.

For example, based on the displayed electrical activity of the heart 402 in the view shown in FIG. 5 and the ECG signals displayed in the ECG window in FIG. 5, the user may further change the view (i.e., orientation) of the heart 402 shown in FIG. 5 to the view (i.e., orientation) of the heart 402 shown in FIG. 6. Then, based on the displayed electrical activity of the heart 402 in the view shown in FIG. 6, the user may determine (e.g., visualize) a ROI (i.e., an anatomical region of the heart 402) as potentially causing an irregular heart rhythm and, therefore, be a potential region targeted for ablation. Accordingly, the user may indicate the location of the anatomical region of the heart by positioning the marked area 602 at the location on the heart 402 shown in FIG. 6.

As shown in the display 600 at FIG. 6, the ECG window 406 has been changed to display 13 electrical signals corresponding to the ECG signals acquired, via 13 electrodes, from the areas located at the surface of the heart 402 in the marked area 602. Accordingly, because a smaller number of ECG signals are displayed, it is easier to determine activation sequences or patterns in the ROI from the displayed ECG signals. For example, as indicated by the lines 604 in the ECG window 406 in FIG. 5, activation patterns, such as a RAP source, may be identified by viewing the ECG signals in the ECG window 406.

The second example is now described with reference to FIGS. 7-9. As described above with regard to block 304, the user input may include an indication of a position of a 2D plane on the map of the heart 402 which defines the ROI (i.e., an anatomical region of the heart 402 on the map). FIGS. 7-9 illustrate the change in the number of displayed ECG signals based on the number of areas of the heart 402 that are located in the anatomical region of the heart defined by the 2D plane 802.

FIG. 7 shows an example display 700 of a map of heart 402 and the electrical signals acquired from the heart 402 over a predetermined time interval. As shown in FIG. 7, 60 ECG signals are displayed in the ECG window 406. FIG. 8 shows an example display 800 which includes a 2D plane 802 at a first position used to define an anatomical region 804 of the heart 402 shown in FIG. 7 and the electrical signals acquired from areas of the heart 402 located in the 2D plane 802. FIG. 9 shows an example display 900 which includes the 2D plane 802 at a second position used to define a second anatomical region 804 of the heart 402 shown in FIG. 8 and the electrical signals acquired from areas of the heart 402 located in the 2D plane 802.

In the example shown in FIGS. 7-9, the user input indicates a position of the 2D plane 802 on the map which defines the anatomical region. As shown in FIG. 8, a smaller number (i.e., 40) of electrical signals are acquired at the anatomical region 804 defined by the position of the 2D plane 802 than the number (i.e., 60) of electrodes acquired at the heart 402 shown in FIG. 7. That is, the 40 electrodes are used to acquire the electrical signals from 40 corresponding different areas of the heart 402, each of which is located in the anatomical region 804 defined by the 2D plane 802.

In one embodiment, the position of the 2D plane 802 may be changed by changing the view (i.e., orientation) of the heart 402. For example, the orientation of the heart 402 may be changed from the orientation of the heart 402 in display 700 to the orientation of the heart in display 800. A user may change the orientation of the heart 402, for example, by rotating the heart 402 about an axis (not shown). The axis may be a horizontal axis, a vertical axis or an axis in any direction in 3D space. Accordingly, a user may rotate the heart 402 in any direction between 0 and 360 degrees in 3D space.

In another embodiment, the position of the 2D plane 802 may be changed by moving the 2D plane 802 relative to the heart 402. For example, the position of the heart 402 may be changed from the position of the heart 402 in display 800 of FIG. 8 to the position of the heart 402 in display 900 of FIG. 9 by moving the 2D plane 802 relative to the heart 402.

As shown in FIGS. 8 and 9, the number of electrical signals displayed is further reduced from the change in the position of the 2D plane defining the anatomical regions 804, 904. Evidence of the reduced number of displayed electrical signals can be seen by the omission of area 806 (shown in FIG. 8) from the anatomical region in FIG. 9. The number of electrodes (i.e., 20) used to acquire the electrical signals from areas the anatomical region 904 in the 2D plane 802 in FIG. 9 is less than the number of electrodes (i.e., 40) used to acquire the electrical signals from the anatomical region defined by the 2D plane 802 in FIG. 8.

The anatomical region 904 of the heart 402, defined by the position of the 2D plane 802, is determined. The 20 corresponding electrical signals acquired from areas of the heart 402 in the anatomical region 904 are then determined and correlated ECG signal information is generated for displaying the 20 corresponding electrical signals. The 20 electrical signals, acquired from areas in the anatomical region 904 defined by the 2D plane 802, are displayed in the ECG window 406 shown in FIG. 9.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. An electrocardiogram (ECG) signal correlation and display system comprising:
    memory configured to store:
        ECG data corresponding to a plurality of electrical signals, acquired over time, from different areas of a heart; and
        location data corresponding to acquired location signals indicating locations of each of the different areas of the heart from which the electrical signals are acquired; and
    a processing device configured to:
        generate, from the ECG data and the location data, mapping information for displaying a map of the heart;
        determine a location of an anatomical region of the heart on the map;
        determine which of the plurality of electrical signals are acquired from the anatomical region of the heart;
        generate correlated ECG signal information for displaying the electrical signals determined to be acquired from the anatomical region of the heart and non-correlated ECG signal information for displaying the electrical signals acquired from each of the different areas of the heart; and
        drive a display device to display:
            the map of the heart using the mapping information;
            the plurality of electrical signals acquired from each of the different areas of the heart;
            the electrical signals determined to be acquired from the anatomical region of the heart; and
            the electrical signals determined to be acquired at the anatomical region of the heart without displaying the electrical signals determined not to be acquired from the anatomical region of the heart.

2. The system of claim 1, wherein the processing device is further configured to:
    receive a user input indicating the location of the anatomical region of the heart on the map, and
    determine the location of the anatomical region of the heart on the map based on the user input.

3. The system of claim 2, wherein the user input corresponds to a marked area on a surface of the heart, and
    the processing device is further configured to determine the location of the anatomical region of the heart from the marked area of the heart.

4. The system of claim 1, further comprising a catheter which comprises a plurality of electrodes, disposed at the different areas of the heart, each electrode configured to acquire the electrical signals over time from one of the different areas of the heart,
    wherein the location signals indicate the locations of each of the different areas of the heart by indicating locations of the electrodes disposed at each of the different areas.

5. An electrocardiogram (ECG) signal correlation and display method comprising:
    acquiring ECG data, corresponding to a plurality of electrical signals of a heart acquired over time, via a plurality of electrodes disposed at different areas of the heart;
    acquiring location data, corresponding to acquired location signals indicating locations of each of the different areas of the heart from which the electrical signals are acquired;
    generating, from the ECG data and the location data, mapping information for displaying a map of the heart;
    determining a location of an anatomical region of the heart on the map;
    determining which of the plurality of electrical signals are acquired from the anatomical region of the heart; and
    generating correlated ECG signal information for displaying the electrical signals determined to be acquired from the anatomical region of the heart and non-correlated ECG signal information for displaying the electrical signals acquired from each of the different areas of the heart; and
    driving a display device to display:
        the map of the heart using the mapping information;
        the plurality of electrical signals acquired from each of the different areas of the heart;
        the electrical signals determined to be acquired from the anatomical region of the heart; and the electrical signals determined to be acquired at the anatomical region of the heart without displaying the electrical signals determined not to be acquired from the anatomical region of the heart.

6. The method of claim 5, further comprising:
receiving a user input indicating the location of the anatomical region of the heart on the map, and
determining the location of the anatomical region of the heart on the map based on the user input.

7. The method of claim 6, wherein the user input corresponds to a marked area on a surface of the heart, and
the method further comprises determining the location of the anatomical region of the heart from the marked area of the heart.

8. A non-transitory computer readable medium having instructions for causing a computer to perform a method comprising:
acquiring ECG data, corresponding to a plurality of electrical signals of a heart acquired over time, via a plurality of electrodes disposed at different areas of the heart;
acquiring location data, corresponding to acquired location signals indicating locations of each of the different areas of the heart from which the electrical signals are acquired;
generating, from the ECG data and the location data, mapping information for displaying a map of the heart;
determining a location of an anatomical region of the heart on the map;
determining which of the plurality of electrical signals are acquired from the anatomical region of the heart; and
generating correlated ECG signal information for displaying the electrical signals determined to be acquired from the anatomical region of the heart and non-correlated ECG signal information for displaying the electrical signals acquired from each of the different areas of the heart; and
driving a display device to display:
the map of the heart using the mapping information;
the plurality of electrical signals acquired from each of the different areas of the heart;
the electrical signals determined to be acquired from the anatomical region of the heart; and
the electrical signals determined to be acquired at the anatomical region of the heart without displaying the electrical signals determined not to be acquired from the anatomical region of the heart.

9. An electrocardiogram (ECG) signal correlation and display system comprising:
memory configured to store:
ECG data corresponding to a plurality of electrical signals, acquired over time, from different areas of a heart; and
location data corresponding to acquired location signals indicating locations of each of the different areas of the heart from which the electrical signals are acquired; and
a processing device configured to:
generate, from the ECG data and the location data, mapping information for displaying a map of the heart;
determine a location of an anatomical region of the heart on the map;
determine which of the plurality of electrical signals are acquired from the anatomical region of the heart;
generate correlated ECG signal information for displaying the electrical signals determined to be acquired from the anatomical region of the heart;
receive a user input indicating the location of the anatomical region of the heart on the map and corresponding to a position of a plane on the map which defines the anatomical region of the heart; and
determine the location of the anatomical region of the heart on the map by the position of the plane on the map.

10. The system of claim 9, wherein the processing device is further configured to receive a second user input, which is an instruction to move the heart on the map about an axis from a first orientation to a second orientation, and
the processing device is further configured to determine the location of the anatomical region of the heart at the second orientation.

11. An electrocardiogram (ECG) signal correlation and display method comprising:
acquiring ECG data, corresponding to a plurality of electrical signals of a heart acquired over time, via a plurality of electrodes disposed at different areas of the heart;
acquiring location data, corresponding to acquired location signals indicating locations of each of the different areas of the heart from which the electrical signals are acquired;
generating, from the ECG data and the location data, mapping information for displaying a map of the heart;
determining a location of an anatomical region of the heart on the map;
determining which of the plurality of electrical signals are acquired from the anatomical region of the heart; and
generating correlated ECG signal information for displaying the electrical signals determined to be acquired from the anatomical region of the heart;
receiving a user input indicating the location of the anatomical region of the heart on the map and corresponding to a position of a plane on the map which defines the anatomical region of the heart; and
determining the location of the anatomical region of the heart on the map by the position of the plane on the map.

12. The method of claim 11, wherein the user input is an instruction to move the plane relative to the heart to the position on the map, and
the method further comprises determining the location of the anatomical region of the heart defined by the position of the plane on the map.

13. The method of claim 11, wherein the processing device is further configured to receive a second user input, which is an instruction to move the heart on the map about an axis from a first orientation to a second orientation, and
the method further comprises determining the location of the anatomical region of the heart at the second orientation.

14. A non-transitory computer readable medium having instructions for causing a computer to perform a method comprising:
acquiring ECG data, corresponding to a plurality of electrical signals of a heart acquired over time, via a plurality of electrodes disposed at different areas of the heart;
acquiring location data, corresponding to acquired location signals indicating locations of each of the different areas of the heart from which the electrical signals are acquired;
generating, from the ECG data and the location data, mapping information for displaying a map of the heart;

determining a location of an anatomical region of the heart on the map;

determining which of the plurality of electrical signals are acquired from the anatomical region of the heart; and generating correlated ECG signal information for displaying the electrical signals determined to be acquired from the anatomical region of the heart;

receiving a user input indicating the location of the anatomical region of the heart on the map and corresponding to a position of a plane on the map which defines the anatomical region of the heart; and determining the location of the anatomical region of the heart on the map by the position of the plane on the map.

* * * * *

UNITED STATES PATENT AND TRADEMARK OFFICE
CERTIFICATE OF CORRECTION

| | |
|---|---|
| PATENT NO. | : 10,542,888 B2 |
| APPLICATION NO. | : 15/722667 |
| DATED | : January 28, 2020 |
| INVENTOR(S) | : Ziyad Zeidan et al. |

It is certified that error appears in the above-identified patent and that said Letters Patent is hereby corrected as shown below:

On the Title Page
In Item (72), under "Inventors", in Column 1, Line 1, delete "Zemmer (IL);" and insert -- Zemer (IL); --, therefor.
In Item (72), under "Inventors", in Column 1, Line 2, delete "Tivon (IL)" and insert -- Tiv'on (IL) --, therefor.

In the Specification
In Column 2, Line 63, delete "the" and insert -- of the --, therefor.

In the Claims
In Column 12, Line 55, in Claim 5, delete "heart; and" and insert -- heart; --, therefor.
In Column 13, Line 31, in Claim 8, delete "heart; and" and insert -- heart; --, therefor.
In Column 14, Line 31, in Claim 11, delete "heart; and" and insert -- heart; --, therefor.
In Column 15, Line 4, in Claim 14, delete "heart; and" and insert -- heart; --, therefor.

Signed and Sealed this
Twenty-fourth Day of January, 2023

Katherine Kelly Vidal
*Director of the United States Patent and Trademark Office*